United States Patent [19]

Oe et al.

[11] Patent Number: 5,001,137

[45] Date of Patent: Mar. 19, 1991

[54] PYRIDINE COMPOUNDS AND PHARMACEUTICAL USE THEREOF

[75] Inventors: Takanori Oe; Yuji Ono, both of Oita; Kazuyuki Kawasaki, Fukuoka; Tohru Nakajima, Oita, all of Japan

[73] Assignee: Yoshitomi Pharmaceutical Industries, Ltd., Osaka, Japan

[21] Appl. No.: 407,010

[22] Filed: Sep. 14, 1989

[30] Foreign Application Priority Data

Sep. 14, 1988 [JP] Japan .................................. 63-231261
Jan. 17, 1989 [JP] Japan ....................................... 1-8971

[51] Int. Cl.$^5$ ..................... A61K 31/44; C07D 213/50; C07D 213/63; C07D 213/74; C07D 401/06

[52] U.S. Cl. ..................................... 514/342; 514/343; 514/341; 514/340; 514/339; 514/338; 514/337; 514/336; 514/335; 514/334; 514/333; 514/332; 514/318; 514/316; 514/254; 514/253; 514/252; 514/237.2; 514/236.8; 514/236.5; 514/236.2; 514/235.8; 514/235.2; 514/234.5; 514/233.8; 514/233.5; 514/232.8; 514/232.5; 514/232.2; 514/231.8; 514/231.5; 514/228.2; 514/227.8; 514/212; 514/218; 514/348; 514/349; 514/350; 514/352; 514/346; 540/524; 540/575; 546/187; 546/194; 546/281; 546/280; 546/279; 546/278; 546/277; 546/276; 546/256; 546/262; 546/261; 546/275; 546/274; 546/273; 546/272; 546/270; 546/271; 546/283; 546/284; 546/291; 546/309; 546/310; 546/298; 546/297; 546/296; 544/58.6; 544/78; 544/79; 544/80; 544/82; 544/120; 544/121; 544/114; 544/130; 544/131

[58] Field of Search ............... 546/309, 310, 298, 297, 546/296; 514/336, 348, 349, 350, 352, 346, 337, 338, 339, 340, 341, 342, 343, 212, 218, 227.8, 228.2, 231.5, 231.8, 232.2, 232.5, 232.8, 233.5, 233.8, 234.5, 235.2, 235.8, 236.2, 236.5, 236.8, 237.2, 252, 253, 254, 316, 318, 332, 333, 334, 335

[56] References Cited

U.S. PATENT DOCUMENTS 4,061,642 12/1977 Fleckenstein et al. ........... 260/295.5

Primary Examiner—John M. Ford
Attorney, Agent, or Firm—Sughrue, Mion, Zinn, Macpeak & Seas

[57] ABSTRACT

A novel pyridine compound of the formula

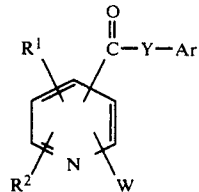

wherein each symbol is as defined in the specification, or a salt thereof which exhibit inhibitory activity or prolylendopeptidase and a pharmaceutical use thereof are disclosed.

3 Claims, No Drawings

PYRIDINE COMPOUNDS AND PHARMACEUTICAL USE THEREOF

FIELD OF THE INVENTION

This invention relates to pyridine compounds and their salts which exhibit inhibitory activity on prolylendopeptidase and are useful for the treatment of amnesia.

BACKGROUND OF THE INVENTION

It is known that prolylendopeptidase acts on substances P, TRH (thyrotropin releasing hormone) and neurotensin which have been deemed as neural transmitting substance, and vasopressin which is considered to be concerned with memory, and inactivates them. Nakajima et al and Yoshimoto et al found that the compounds which inhibit prolylendopeptidase activity could prevent experimental amnesia in rats induced by scopolamine and presumed that prolylendopeptidase-inhibitory agents were concerned with the consolidation of memory (Nakajima et al, Folia Pharmacologica Japonica, vol. 82, p 154 (1983), Yoshimoto et al, Seikagaku, vol. 55, p 831 (1983)). This suggests a possibility that prolylendopeptidase-inhibitory agents can be used as anti-amnesiac drugs.

Hitherto, as prolylendopeptidase-inhibitory agents, as reported in Japanese Patent Applications Laid-open (Kokai) Nos. 130579/1988 and 162672/1988, known are proline derivatives having a peptide bond.

On the other hand, in Japanese Patent Applications Laid-open (Kokai) Nos. 100765/1981 and 91172/1986 and Journal of Medicinal Chemistry, vol. 8, p 722 (1965), pyridine compounds substituted by a benzoyl group or other groups are reported. Further, anti-anxietic or sedative ω-aminoalkoxybenzoylthiophene compounds are disclosed in Japanese Patent Application Laid-open (kokai) No. 56476/1982.

The present inventors have conducted intensive studies for the purpose of developing novel prolylendopeptidase-inhibitory agents in of a non-peptide type.

As the result, the present inventors found novel pyridine derivatives possessing an excellent inhibitory activity on prolylendopeptidases which resulted in the completion of this invention.

SUMMARY OF THE INVENTION

The object of this invention is to provide novel pyridine compounds possessing an excellent inhibitory activity on prolylendopeptidase.

Another object of this invention is to provide a pharmaceutical use of such pyridine compounds.

DETAILED DESCRIPTION

This invention relates to pyridine compounds of the formula

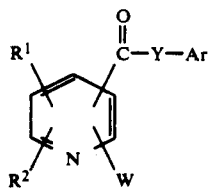

[wherein $R^1$ and $R^2$ are the same or different and respectively mean hydrogen, a halogen, an alkyl, an alkoxy or an optionally substituted phenyl; Ar means an optionally substituted aryl or heteroaryl; Y means a single bond or an alkylene which may have double bond(s) in the chain; W means a group of the formula

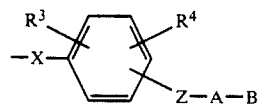

(wherein $R^3$ and $R^4$ are the same or different and respectively mean hydrogen, a halogen, an alkyl, an alkoxy or an optionally substituted phenyl, X means —O—, —S— or —N($R^5$)— (wherein $R^5$ means hydrogen, an alkyl or an acyl), Z means a single bond, —O—, —S—, —N($R^6$)— (wherein $R^6$ means hydrogen, an alkyl or an acyl) or —CON($R^7$)— (wherein $R^7$ means hydrogen, an alkyl or an acyl), A means an alkylene, B means an alkoxycarbonyl, carboxyl, hydroxyl group, —N($R^8$)($R^9$) (wherein $R^8$ and $R^9$ are the same or different and respectively mean hydrogen, an alkyl, a hydroxyalkyl, an acyl or an optionally substituted aralkyl or heteroaralkyl or conbinedly means a group, forming taken together with the adjacent nitrogen, a heterocyclic group) or —CON($R^{10}$)($R^{11}$) (wherein $R^{10}$ and $R^{11}$ are the same or different and respectively mean hydrogen, an alkyl, a hydroxyalkyl, an acyl or an optionally substituted aralkyl or heteroaralkyl, or combinedly mean a group forming, taken together with the adjacent nitrogen, a heterocyclic group)), a group of the formula

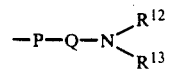

(wherein $R^{12}$ and $R^{13}$ are the same or different and respectively mean hydrogen, an alkyl, a hydroxyalkyl, an acyl, 2-dimethylaminoethyl, an optionally substituted phenyl or an optionally substituted aralkyl or heteroaralkyl, or combinedly mean a group forming, taken together with the adjacent nitrogen atom, a heterocyclic group, P means —O—, —S(O)p— (wherein p means an integer of 0 to 2), —N($R^{14}$)— (wherein $R^{14}$ means hydrogen, an alkyl or an acyl) or —N($R^{15}$)CO— (wherein $R^{15}$ means hydrogen, an alkyl or an acyl), Q means an alkylene having not less than 5 carbon atoms, a cyclic alkylene, an alkylene having not less than 4 carbon atoms which has an interposing oxygen or a sulfur therein or an alkylene having not less than 5 carbon atoms which has carbonyl group at the terminus, with the proviso that Q means an alkylene having not less than 3 carbon atoms, when P is —N($R^{15}$)CO—) or a group of the formula

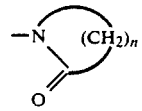

(wherein n means an integer of 3 to 5)], and their salts and further pharmaceutical uses thereof.

Throughout the present specification, the halogen means chlorine, bromine, fluorine or iodine; the alkyl means a straight-chain or branched chain alkyl having 1 to 8 carbon atoms, exemplified by methyl, ethyl, propyl, isopropyl, butyl, isobutyl, tert-butyl, pentyl, hexyl, octyl and the like; the alkoxy means a straight-chain or branched chain alkoxy having 1 to 8 carbon atoms, exemplified by methoxy, ethoxy, propoxy, isopropoxy, butoxy, isobutoxy, tert-butoxy, pentyloxy, hexyloxy, octyloxy and so on; the optionally substituted phenyl means phenyl or a phenyl which has 1 to 3 substituent(s) selected from among halogens, alkyls, alkoxys, trifluoromethyl, amino, nitro and cyano (e.g. chlorophenyl, dichlorophenyl, methylphenyl, trimethoxyphenyl, trifluoromethylphenyl, aminophenyl, nitrophenyl, cyanophenyl); the optionally substituted aryl means phenyl, naphthyl, or a phenyl or naphthyl which has 1 to 3 substituent(s) selected from among hydroxy, 2-oxopyrrolidinyl, halogens, alkyls, alkoxys, trifluoromethyl, alkylthios (straight-chain or branched chain alkylthios having 1 to 8 carbon atoms exemplified by methylthio, ethylthio, propylthio, isopropylthio, butylthio, isobutylthio, tertbutylthio, pentylthio, hexylthio, octylthio and the like), alkylsulfinyls (straight-chain or branched chain alkylsulfinyls having 1 to 8 carbon atoms, exemplified by methylsulfinyl, ethylsulfinyl, propylsulfinyl, isopropylsulfinyl, butylsulfinyl, isobutylsulfinyl, tert-butylsulfinyl, pentylsulfinyl, hexylsulfinyl, octylsulfinyl and the like), alkylsulfonyls (straight-chain or branched chain alkylsulfonyls having 1 to 8 carbon atoms, exemplified by methylsulfonyl, ethylsulfonyl, propylsulfonyl, isopropylsulfonyl, butylsulfonyl, isobutylsulfonyl, tert-butylsulfonyl, pentylsulfonyl, hexylsulfonyl, heptylsulfonyl, octylsulfonyl and the like), and phenyls and naphthyls which may have 1 to 3 substituents selected from among amino, nitro and cyano (e.g., chlorophenyl, difluorophenyl, methylphenyl, trimethoxyphenyl, trifluoromethylphenyl, methylthiophenyl, methylsulfinylphenyl, aminophenyl, nitrophenyl, cyanophenyl, methoxynaphthyl); the optionally substituted heteroaryl means furyl, thienyl, pyrrolyl, imidazolyl, oxazolyl, thiazolyl, isoxazolyl, isothiazolyl, pyrazolyl, oxadiazolyl, thiadiazolyl, pyridyl, pyridazinyl, pyrazinyl, indolyl, benzimidazolyl, benzoxazolyl, benzothiazolyl or the like, or a furyl, a thienyl, a pyrrolyl, an imidazolyl, an oxazolyl, a thiazolyl, an isoxazolyl, an isothiazolyl, a pyrazolyl, an oxadiazolyl, a thiazolyl, a pyridyl, a pyridazinyl, a pyrazinyl, an indolyl, a benzimidazolyl, a benzoxazolyl, a benzothiazolyl or the like, each, of which has 1 to 3 substituent(s) selected from among formyl, morpholino, methoxycarbonylmethyl, halogens, alkyls, alkoxys, trifluoromethyl, alkylthios, alkylsulfinyls, alkylsulfonyls, amino, nitro and cyano; the acyl means a straight-chain or branched chain alkanoyl having 2 to 5 carbon atoms, exemplified by acetyl, propionyl, butyryl, pivaloyl, valeryl and the like; the alkoxy moiety in the alkoxycarbonyl means a straight-chain or branched chain alkoxy having 1 to 8 carbon atoms, exemplified by methoxycarbonyl, ethoxycarbonyl, propoxycarbonyl, isopropoxycarbonyl, butoxycarbonyl, isobutoxycarbonyl, tert-butoxycarbonyl, pentyloxycarbonyl, hexyloxycarbonyl, octyloxycarbonyl and the like; the alkyl moiety of the hydroxyalkyl means a straight-chain or branched chain alkyl having 1 to 8 carbon atoms, exemplified by hydroxymethyl, 2-hydroxyethyl, 3-hydroxypropyl, 4-hydroxybutyl, 5-hydroxypentyl, 6-hydroxyhexyl, 8-hydroxyoctyl and the like; the optionally substituted aralkyl or heteroaralkyl means benzyl, 2-phenylethyl, 1-phenylethyl, 3-phenylpropyl, 4-phenylbutyl, 6-phenylhexyl, 8-phenyloctyl, 2-pyridylmethyl, 3-pyridylmethyl, 4-pyridylmethyl, 2-(2-pyridyl)ethyl or the like each of which may have 1 to 3 substituent(s) selected from among halogens, alkyls, alkoxys, trifluoromethyl, amino, nitro and cyano; the heterocyclic group formed combinedly taken together with the adjacent nitrogen atom means, 3-thiazolidinyl 1-pyrrolidinyl, 2-oxo-1-pyrrolidinyl, piperidino, 1-piperazinyl, 1-homopiperazinyl, morpholino, thiomorpholino (which may be substituted by formyl, an alkyl, an acyl benzyl, dimethylamino, 2-hydroxyethyl, methoxycarbonyl, hydroxymethyl, bis(4-fluorophenyl)methyl, morpholinocarbonylmethyl or trifluoromethylphenyl, or the like); the alkylene which may have double bond(s) in the chain means a straight-chain or branched chain alkylene having 1 to 8 carbon atoms, exemplified by methylene, ethylene, trimethylene, propylene, tetramethylene, pentamethylene, hexamethylene, octamethylene, vinylene, butadiene, hexatriene and the like; the alkylene means a straight-chain or branched chain alkylene having 1 to 8 carbon atoms, exemplified by methylene, ethylene, trimethylene, propylene, tetramethylene, pentamethylene, hexamethylene, octamethylene or the like; the alkylene having not less than 5 carbon atoms means a straight-chain or branched chain alkylene, exemplified by methyltetramethylene, pentamethylene, hexamethylene, octamethylene, decamethylene, dodecamethylene, tetradecamethylene, octadecamethylene and the like; the cyclic alkylene means cyclopropylene, cyclopentylene, cyclohexylene, or cyclohexylmethylene and the like; the alkylene having not less than 4 carbon atoms which has an interposing oxygen or sulfur therein means —CH$_2$O(CH$_2$)$_3$—, —(CH$_2$)2S(CH$_2$)3— or the like; the alkylene having not less than 5 carbon atoms and carbonyl group at the terminus means 1-oxohexamethylene, 1-oxooctamethylene, 1-oxodecamethylene and the like.

The preferable compounds of the formula (I) of this invention include, for example, 2-[2-(3-dimethylaminopropyl)1-methylethylthio]-3-(2-thenoyl)pyridine, 2-(6-dimethylaminohexylthio)-3-(2-thenoyl)pyridine, 2-(7-dimethylaminoheptyl-thio)-3-(2-thenoyl)pyridine, 2-[2-(3-dimethylaminopropyl)ethylthio]-3-(2-thenoyl)pyridine, 2-[2-(6-dimethylaminohexylthio)ethylthio]-3-(2-thenoyl)pyridine, 2-[2-(6-dimethylamino-hexylthio)-1-methylethylthio]-3-(2-thenoyl)pyridine, 2-[2-(6-dimethylaminohexylthio)-1,1-dimethylethylthio]-3-(2-thenoyl)pyridine, 2-(7-dimethylamino-1-methylheptylthio)-3-(2-thenoyl)pyridine, 2-(6-dimethylaminohexylthio)-6-methyl-3-(2-thenoyl)pyridine, 2-(6-diethylaminohexylthio)-6-isopropyl-3-(2-thenoyl)pyridine, 3-benzoyl-2-[2-(3-dimethylaminopropylthio)-1-methylethylthio]-6-methylpyridine, 2-(6-dimethylaminohexylthio)-6-isopropyl-3-(5-methyl-2-thenoyl)pyridine, 2-[6-(N-benzyl-N-methylamino)hexylthio]-3-(2-thenoyl)-6-isopropylpyridine, 2-[6-(N-(3,4-dimethoxybenzyl)-N-methylamino)hexylthio]-3-(2-thenoyl)-6-isopropylpyridine, 2-(6-benzylaminohexylthio-3-(2-thenoyl)-6-isopropylpyridine, 2-(6-ethylamino-hexylthio)-3-(2-thenoyl)-6-isopropylpyridine, 2-[6-(4-benzylpiperidino)hexylthio]-3-(2-thenoyl)-6-isopropylpyridine, 2-[6-(4-dimethylaminopiperidino)-hexylthio]-3-(2-thenoyl)-6-isopropylpyridine, 2-[6-(2-phenylethylamino)hexylthio]-3-(2-thenoyl)-6-isopropylpyridine and 2-[6-(N-(2-dimethylaminoethyl)-N-methylamino)hexylthio-3-(2-thenoyl)-6-isopropylpyridine or their pharmaceutically acceptable salts.

The pyridine compounds of the present invention can be produced by the following methods.

Method 1:

A method which comprises reacting a compound of the general formula

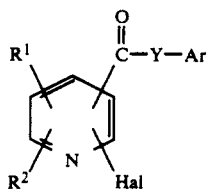 (II)

wherein Hal stands for a halogen and the other symbols are as defined above, with a compound of the general formula

 (III)

wherein W is of the same meaning as defined above.

In this reaction, in the case where X and P are oxygen, sulfur, or nitrogen substituted by an acyl or an alkoxycarbonyl, it is preferable to react after substituting an alkali metal for the active hydrogen with sodium hydride, sodium amide, sodium methoxide, sodium hydroxide, potassium hydroxide, or the like. In the case where X and P are a basic nitrogen atom, preferably the reaction is conducted in the presence of a tertiary amine (triethylamine, methylmorpholine, dimethylaniline, pyridine, etc.) or an inorganic base (sodium bicarbonate, sodium carbonate, potassium carbonate, etc.) as the deacidifying agent. The reaction can be generally conducted in a solvent. As such solvents to be used, mention may be made of dimethylformamide, dimethyl sulfoxide, toluene, xylene, $C_1$-$C_4$ alkanols and the like. Though the reaction temperature is not particularly limited, the reaction can be completed fully at 0°–150° C.

Method 2:

A method which comprises reacting a compound of the general formula:

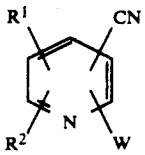 (IV)

wherein each of the symbols is as defined above, with a Grignard reagent of the general formula

 (V)

wherein Hal stands for a halogen and Ar is as defined above or an organic lithium compound of the formula Ar—Li (VI)

wherein Ar is as defined above.

This method can be conducted by reacting in an anhydrous solvent such as ether, tetrahydrofuran, dioxane, benzene, toluene or a mixture thereof in accordance with a conventional method, followed by hydrolysis.

A starting compound of the general formula (IV) can be produced by reacting a compound of the general formula

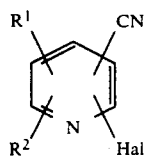 (a)

wherein each of the symbol is as defined above, with a compound of the general formula

H—W wherein W is as defined above.

Method 3

A compound of the general formula (I) wherein Y is —$(CH_2)_n$— can be obtained by reducing a compound of the general formula

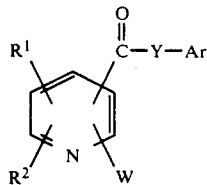 (VII)

wherein each of symbols is as defined above except that Y stands for an alkylene which has double bond in the chain, in accordance with a conventional method.

Method 4

A compound of the general formula (I) wherein W is a group of the formula (i) can be produced by the following methods.

(a) A method which comprises reacting a compound of the formula

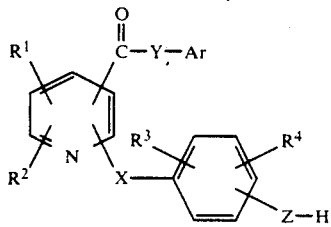 (VIII)

wherein each of the symbols is as defined above except that Z stands for a single bond, with a compound of the general formula Hal—A—B (IX)

wherein Hal stands for a halogen and the other symbols are as defined above.

In this reaction, in the case where a compound of the general compound (VIII) wherein Z is oxygen, sulfur, an acyl or a nitrogen substituted by an acyl or an alkoxycarbonyl, preferably the reaction is carried out by substituting an alkali metal for the activated hydrogen with sodium hydride, sodium amide, sodium methoxide, sodium hydroxide, potassium hydroxide or the like. In the case of a compound of the general formula (VIII) wherein Z is a basic nitrogen atom, preferably the reaction is conducted in the presence of a deacidifying agent such as a tertiary amine (triethylamine, methylmorpholine, dimethylaniline, pyridine, etc.) or an inorganic base (sodium bicarbonate, sodium carbonate, potassium carbonate, etc.). The reaction can generally be conducted in a solvent, which is exemplified by dimethylformamide, acetone, toluene, xylene, a $C_1$-$C_4$ alkanol or the like. The reaction temperature is not limited and the reaction can be completed sufficiently at 0°–150°.

The starting compounds of the general formula (VIII) can be produced by reacting a compound of the general formula

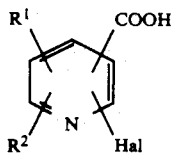 (c)

wherein each of the symbols is as defined above, with a compound of the general formula

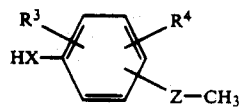 (d)

wherein each of the symbols is as defined above except that X and Z are the same or different and respectively stand for —O—, or —S—, converting the thus obtained compound of the general formula

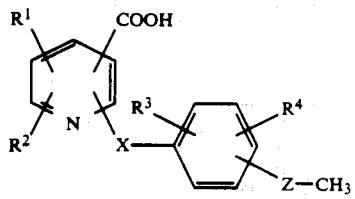 (e)

wherein each of the symbols is as defined above in (c) and (d), into the corresponding acid chloride with, for example, thionyl chloride, converting the corresponding acetyl compound by reacting with ethoxy magnesium•diethyl malonate, reacting with a compound of the general formula

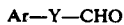 Ar—Y—CHO (f)

wherein each of the symbols is as defined above except that Y stands for an alkylene having double bond(s) in the chain, and then treating thus obtained compound of the general formula

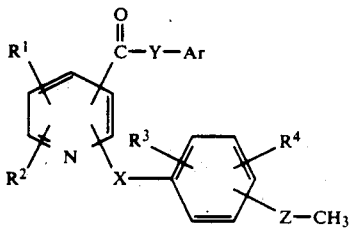 (g)

wherein each of the symbols is as defined above in the formulae (c), (d) and (f), with aluminium chloride alone or with the use of aluminium chloride and 1-butanethiol in combination.

A starting compound of the general formula (VIII) can also be obtained by reacting a compound of the general formula (c) with thionyl chloride to obtain the acid chloride, converting the same through Friedel-Crafts reaction into a compound of the general formula

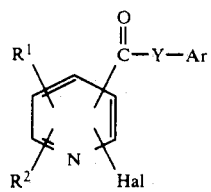 (h)

wherein each of symbols is as defined above except that Y stands for a single bond, reacting with a compound of the general formula (d) to obtain the compound corresponding to a compound of the general formula (g) wherein Y stands for a single bond, followed by a demethylation reaction of the obtained compound in the same manner as mentioned above.

Furthermore, a compound of the general formula (VIII) can also be obtained by reacting a compound of the general formula (a) with a compound of the general formula (d), reacting the obtained compound with a compound of the general formula

 Ar—Mg—Hal (j)

wherein each of the symbols is as defined above to obtain the compound corresponding to a compound of the general formula (g) wherein Y is a single bond, followed by the same demethylation reaction as mentioned above.

(b) A method which comprises reacting a compound of the general formula

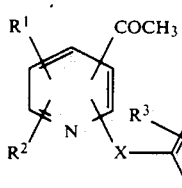 (X)

wherein each of the symbols is as defined above with a compound of the general formula

 Ar—(CH=CH)$_{m-1}$—CHO (XI)

wherein m stands for an integer of 1 to 3 and Ar is as defined above can also be used.

This reaction can be carried out by condensing in the presence of a base (sodium hydroxide, potassium hydroxide, etc.) in a solvent such as methanol or ethanol.

A compound of the general formula (I) wherein W is a group of the formula (ii) (wherein P stands for —N(R$^{15}$)CO—) can be produced by the following methods.

(a) A method which comprises reacting a compound of the general formula

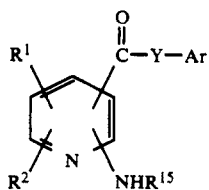 (XII)

wherein each of the symbols is as defined above with a compound of the general formula

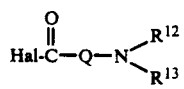 (XIII)

wherein each of the symbols is as defined above.

The reaction is preferably conducted in the presence of a tertiary amine (e.g., triethylamine, methylmorpholine, dimethylaniline, pyridine) as the deacidifying agent. The reaction can generally be generally conducted in a solvent, and, as preferred solvents, mention is made of dimethylformamide, dichloromethane, dichloroethane, chloroform, toluene and the like. The reaction temperature is in the range from 0° C. to the neighborhood of the boiling point of the solvent used, preferably from 0° C. to 50° C.

(b) A method which comprises reacting a compound of the general formula

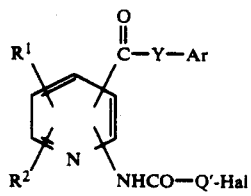 (XIV)

wherein Hal stands for a halogen, Q' stands for an alkylene having not less than 3 carbon atoms and the other symbols are as defined above, with a compound of the general formula

 (XV)

wherein each of the symbols is as defined above can be used.

This reaction can be conducted in the presence of a base in a solvent. As such bases, mention can be made of sodium hydroxide, potassium hydroxide, sodium hydride, sodium methoxide, potassium carbonate, sodium carbonate and the like. As the reaction solvents, there may be mentioned dimethylformamide, ethanol, methanol, acetone and the like. The reaction temperature ranges from 0° C. to the vicinity of the boiling point of the solvent used, preferably from 0° C. to 80° C.

A starting compound of the general formula (XIV) can be produced by reacting a compound of the general formula

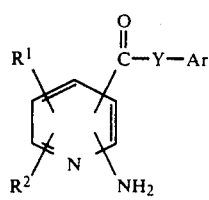 (k)

wherein each of the symbols is as defined above, with a compound of the general formula Hal-Q'-CO-Hal     (l)

wherein each of the symbols is as defined above.

Method 6

A method which comprises subjecting a compound of the general formula

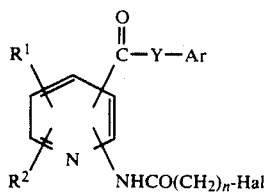 (XVI)

wherein Hal stands for a halogen and the other symbols are as defined above, to ring-closure reaction in the presence of a base.

This reaction can be conducted in a solvent in the presence of a base. As such bases, mention can be made of sodium hydroxide, potassium hydroxide, sodium hydride, potassium hydride, sodium methoxide, sodium ethoxide, potassium carbonate, sodium carbonate and so on. As the reaction solvents, mention can be made of dimethylformamide, ethanol, methanol, acetone, toluene, xylene and the like. The reaction temperature is in the range from 0° C. to the neighborhood of the boiling point of the solvent used, preferably from 0° C. to 80° C.

The thus obtained pyridine compounds of the general formula (I) can be, if necessary, converted into an acid addition salt of an inorganic acid such as hydrochloric acid, hydrobromic acid, or sulfuric acid, or an organic acid such as oxalic acid, fumaric acid, maleic acid, citric acid or tartaric acid. The compounds having a carboxyl group can be converted into their salts such as metal salts with sodium, potassium, calcium, lithium, magnesium, aluminium or the like, amine salts with triethylamine and the like, or salts with amino acids such as lysine, ornithine or the like. The compounds of the general formula (I) can exist as their solvates including hydrates.

Among the compounds of the present invention, those which have asymmetric carbon atoms can exist as their racemic mixtures or optically active isomers.

The compounds of the general formula (I) or their salts of the present invention possess prolylendopeptidase-inhibitory actions which have not been observed in the previously known compounds, and therefor they are of use for prophylaxis and therapy of amnesia.

EXPERIMENTAL EXAMPLE (Measurement of prolylendopeptidase-inhibitory activity)

The prolylendopeptidase-inhibitory activity was estimated, using rat cerebral soluble fractions as the crude enzyme, in accordance with the methods by Yoshimoto et al (Biochem. Biophys. Acta., vol. 569, p 184 (1979)) and Kato et al. (J. Neurochem., vol. 35, p 527 (1980)). That is, a mixture containing 0.1 ml of 0.25 mM succinyl-glycyl-prolylmethylcoumarinamide, 1.15 ml of 0.1M Na/K phosphate buffer solution (pH 7.0), 0.1 ml of the crude enzyme and 0.1 ml of a solution of the compound of the present invention (at the final concentration of dimethylsulfoxide of 0.25%) was incubated at 30° C. for 15 minutes. Thereafter 1.5 ml of 0.1M acetate buffer solution (pH 4.2) was added to terminate the reaction. The fluorescence intensity (a) of the liberated methyl coumarinamide was measured by a fluorophotometer (Ex. 370 nm, Em. 440 nm). At the same time, the fluorescence intensity (b) of the control comprising a dimethylsulfoxide solution alone (at the final concentration of 0.25%) instead of the compound of the present invention was measured, and the prolylendopeptidase-inhibitory rate was calculated in accordance with the following formula and the concentration at which 50% of inhibition ($IC_{50}$) can be attained was estimated.

Inhibition (%) = {(b−a)/b} × 100

The results are as shown in Table 1.

TABLE 1

| Example No. | Prolylendopeptidase-inhibitory activity ($IC_{50}$, μM) |
|---|---|
| 1 | 0.014 |
| 2 | 0.030 |
| 4 | 0.060 |
| 5 | 0.0095 |
| 6 | 0.078 |
| 13 | 0.055 |
| 17 | 0.0045 |
| 18 | 0.0095 |
| 19 | 0.0045 |
| 20 | 0.0045 |
| 21 | 0.0055 |
| 22 | 0.011 |
| Known Compound | 1800 |

The known compound is 3-(4-chlorobenzoyl)-2-(3-dimethylaminepropoxy)pyridine.

From the results of the experiment as shown above, the compounds of the present invention exhibit excellent prolylendopeptidase-inhibitory activity and thus are useful for the prophylaxis and treatment of ammnesia.

When the compounds (I) and their acid addition salts of the present invention are used as the above-mentioned medicaments, they can be orally or parenterally administered alone or in a form exemplified by powders, granules, tablets, capsules, injections and so on as an admixture of the therapeutically effective amount of the compound of this invention with appropriate pharmaceutically acceptable additives such as carriers, excipients, diluents and the like. While the dosage varies depending upon the objective disease, symptom and the compound to be used, the daily dosage in usually in the range from about 1 to about 1000 mg per human adult in the case of oral administration.

PHARMACEUTICAL EXAMPLE

| | |
|---|---|
| Compound of Example 1 | 10.0 mg |
| Lactose | 50.0 mg |
| Corn starch | 15.5 mg |
| Fine crystalline cellulose | 20.0 mg |
| Talc | 4.0 mg |
| Magnesium stearate | 0.5 mg |
| | 100.0 mg |

After the compound of Example 1, lactose, corn starch and fine crystalline cellulose are mixed in a kneader, a binder of 5% corn starch is added to the mixture. The mixture is granulated and dried.

The dried granules are screened by passing them through a sieve of 24 mesh. Talc and magnesium stearate are mixed with screened granules and the mixture is formulated into tablets of 100 mg per tablet with a punch of a diameter of 7 mm.

The present invention is specifically explained by illustrating working examples and reference examples, which should not be construed as limiting the present invention as follows:

REFERENCE EXAMPLE 1

2-Chloronicotinic acid and 4,5-dichloro-2-methoxyphenol are reacted in the presence of potassium carbonate in dimethylformamide to give 2-(4,5-dichloro-2-methoxyphenoxy)nicotinic acid, which is reacted with thionyl chloride in dichloroethane to be converted into the acid chloride. This acid chloride is reacted with ethoxymagnesium.diethyl malonate in a mixed solvent of chlorobenzene and ethanol, followed by treatment with conc. hydrochloric acid and acetic acid to obtain the acetyl compound. This acetyl compound is reacted with benzaldehyde in the presence of a small amount of sodium hydroxide in ethanol to give 2-(4,5-dichloro-2-methoxyphenoxy)-3-cinnamoylpyridine. This compound is treated with aluminium chloride to give 2-(4,5-dichloro-2-hydroxyphenoxy)-3-cinnamoylpyridine.

REFERENCE EXAMPLE 2

2-Chloronicotinic acid is reacted with thionyl chloride in dichloroethane to give the acid chloride compound, which is subjected to Friedel-Crafts reaction with thiophene with the use of tin chloride in dichloroethane to give 2-chloro-3-(2-thenoyl)pyridine. The obtained compound is reacted with 4-methoxyphenol in the presence of sodium hydride in dimethylformamide to give 2-(4-methoxyphenoxy)-3-(2-thenoyl)pyridine, which is subjected to demethylation reaction with the use of aluminium chloride and 1-butanethiol in dichloromethane to give 2-(4-hydroxyphenoxy)-3-(2-thenoyl)-pyridine.

REFERENCE EXAMPLE 3

2-Chloro-3-cyanopyridine is reacted with 4-methoxyphenol in the presence of sodium hydride in dimethylformamide to give 2-(4-methoxyphenoxy)-3-cyanopyridine, which is subjected to Grignard reaction with 2-bromothiophene in a mixed solvent of ether and benzene, followed by treatment with hydrochloric acid to give 2-(4-methoxyphenoxy)-3-(2-thenoyl)pyridine. The thus obtained compound is subjected to demethylation reaction with the use of aluminium chloride and 1-butanethiol in dichloromethane to give 2-(4-hydroxyphenoxy)-3-(2-thenoyl)pyridine.

REFERENCE EXAMPLE 4

2-Amino-3-(2-thenoyl)pyridine is reacted with 6-bromohexanoyl chloride in the presence of pyridine in dichloroethane to give 2-(6-bromohexanoylamino)-3-(2-thenoyl)pyridine.

REFERENCE EXAMPLE 5

6-Dimethylaminohexanol is converted into its sodium salt with sodium hydride in toluene, followed by reaction of the sodium salt with 2-chloro-3-cyanopyridine to give 3-cyano-2-(6-dimethylaminohexyloxy)pyridine.

EXAMPLE 1

In 10 ml of dimethylformamide is suspended 0.82 g of 60% sodium hydride, and a solution of 3.4 g of 4-[2-(dimethylamino)ethyl]phenol in 10 ml of dimethylformamide is added dropwise to the suspension. The mixture is stirred at 60° C. for 2 hours. Thereto, a solution of 3.8 g of 2-chloro-3-(2-thenoyl)pyridine in 10 ml of dimethylformamide is added dropwise under ice-cooling.

The mixture is stirred at 70° C. for 2 hours, and then is poured into ice-water, whereto ethyl acetate is added. The ethyl acetate layer is extracted with a dilute hydrochloric acid and the extract is rendered alkaline with potassium carbonate. The isolated oily substance is extracted with ethyl acetate. After the extract is washed with water and dried over anhydrous magnesium sulfate, the solvent is distilled off. The obtained residue is converted into its salt with fumaric acid in ethanol, and the salt is recrystallized from ethanol to give 2-[4-(2-dimethylaminoethyl)phenoxy]-3-(2-thenoyl)pyridine ½ fumarate, m.p. 147°–150° C.

EXAMPLE 2

To 50 ml of dimethylformamide are added 5 g of 2-(4-hydroxyphenoxy)-3-(2-thenoyl)pyridine, 3.5 g of potassium carbonate and 0.5 g of potassium iodide, and the mixture is stirred at room temperature for 30 minutes. Thereto is added 4.1 g of 6-dimethylaminohexyl chloride. The mixture is stirred at 50° C. for 7 hours. Then, the mixture is poured into ice-water, followed by addition of ethyl acetate thereto. The ethyl acetate layer is extracted with hydrochloric acid and the extract is rendered alkaline with potassium carbonate. The isolated oily substance is extracted with ethyl acetate. The extract is washed with water and dried over anhydrous magnesium sulfate. Thereafter, the solvent is distilled off. The residue is converted into the salt with fumaric acid in ethanol. The salt is recrystallized from ethanol to give 2-[4-(6-dimethylaminohexyloxy)phenoxy]-3-(2-thenoyl)pyridine fumarate, m.p. 98°–101° C.

EXAMPLE 3

To 20 ml of dimethylformamide are added 7.7 g of 3-cinnamoyl- 2-(4,5-dichloro-2-hydroxyphenoxy)pyridine and 3.3 g of potassium carbonate, and the mixture is stirred at room temperature for 30 minutes Thereto, 2.8 g of 2-dimethylaminoethyl chloride is added, and the mixture is stirred at 50° C. for 6 hours. The reaction mixture is poured into ice-water, followed by extraction with toluene After the extract is washed with water and dried over anhydrous magnesium sulfate, the solvent is distilled off. The residue is converted into its hydrochloride in isopropyl alcohol and the hydrochloride is recrystallized from isopropyl alcohol to give 3-cinnamoyl-2-[4,5-dichloro-2-(2-dimethylaminoethoxy)phenoxy]pyridine hydrochloride, m.p. 169°–171° C.

EXAMPLE 4

To 30 ml of dimethylformamide are added 3 g of 2-(4-hydroxyphenoxy)-3-(2-thenoyl)-pyridine, 1.7 g of potassium carbonate and 0.3 g of potassium iodide. The mixture is stirred at room temperature for 30 minutes. Thereto is added 1.5 g of 3-dimethylaminopropyl chloride, and the mixture is stirred at 50° C. for 4 hours. Thereafter, the reaction mixture is poured into ice-water, whereto ethyl acetate is added. The ethyl acetate is extracted with a dilute hydrochloric acid and the extract is rendered alkaline with potassium carbonate. The isolated oily substance is extracted with ethyl acetate. After the extract is washed with water and dried over anhydrous magnesium sulfate, the solvent is distilled off. The residue is converted into the salt with fumaric acid in ethanol. The salt is recrystallized from ethanol to give 2-[4-(3-dimethylaminopropoxy)phenoxy]-3-(2-thenoyl)pyridine fumarate ½ hydrate, m.p. 96°–99° C.

EXAMPLE 5

To 50 ml of dimethylformamide are added 4.4 g of 2-mercapto-3-(2-thenoyl)pyridine and 1.5 g of sodium ethoxide The mixture is stirred at room temperature for 30 minutes. Thereto, 4.0 g of 6-dimethylaminohexyl chloride is added, and the mixture is stirred at room temperature for 24 hours. The mixture is poured into ice-water, followed by extraction with toluene. The extract is washed with water, and the solvent is distilled. The residue is subjected to silica gel column chromatography with chloroform as the eluent, and recrystallized from isopropyl ether to give 2-(6-dimethylaminohexylthio)-3-(2-thenoyl)pyridine, m.p. 69°–71° C.

EXAMPLE 6

In 10 ml of toluene is suspended 1.0 g of 60% sodium hydride. To the suspension is added dropwise a solution of 5.7 g of 6-(N-benzyl-N-methylamino)hexanol in 20 ml of toluene. The mixture is stirred at 70° C. for 1 hours.

A solution of 4.1 g of 2-chloro-3-(2-thenoyl)pyridine in 10 ml of toluene is added dropwise to the mixture. The mixture is stirred at 70° C. for 4.5 hours and then is poured into ice-water. Thereto, toluene is added. The toluene layer is extracted with a dilute hydrochloric acid and the extract is rendered alkaline with potassium carbonate. The isolated oily substance is extracted with toluene. The extract is washed with water and dried over anhydrous magnesium sulfate. Thereafter, the solvent is distilled off. The residue is converted into the salt with fumaric acid in ethanol. The fumarate is recrystallized from ethanol to give 2-[6-(N-benzyl-N-methylamino)hexyloxy]-3-(2-thenoyl)pyridine fumarate, m.p. 122°–124° C. (Decomposition)

EXAMPLE 7

To 50 ml of dimethylformamide are added 15 g of 2-chloro-3-(4-chlorobenzoyl)pyridine, 12.2 g of 4-diethylamino-1-methylbutylamine, 10 g of potassium carbonate and 0.1 g of potassium iodide, and the mixture is stirred at 115° C. for 6 hours. Thereafter, the mixture is poured into ice-water, whereto toluene is added. The toluene layer is extracted with a dilute hydrochloric acid and the extract is rendered alkaline with potassium carbonate. The isolated oily substance is extracted with toluene. After the extract is washed with water and dried over anhydrous magnesium sulfate, the solvent is distilled off. The residue is converted into the salt with oxalic acid in isopropyl ether, and the salt is recrystallized from ethyl acetate to give 3-(4-chlorobenzoyl)-2-(4-diethylamino-1-methylbuthylamino)pyridine oxalate, m.p. 72°-73° C.

EXAMPLE 8

To 10 ml of dichloromethane are added 1.02 g of 2-amino-3-(2-thenoyl)pyridine and 0.48 ml of pyridine, whereto a solution of 1.1 g of 4-(2-oxopyrrolidin-1-yl)butyryl chloride in 5 ml of dichloromethane is added dropwise under ice-cooling. The mixture is stirred at room temperature for 2 hours. After the completion of the reaction, water is added to the reaction mixture. The dichloromethane layer is washed with water, and then the solvent is distilled off. The residue is recrystallized from a mixed solvent of ethyl acetate and ethanol to give 2-[4-(2-oxopyrrolidin-1-yl)butyrylamino]-3-(2-thenoyl)pyridine, m.p. 149°-151° C.

To 30 ml of dimethylformamide are added 1.0 g of morpholine, 1.6 g of potassium carbonate and 0.2 g of potassium iodide, whereto 3 g of 2-(6-bromohexanoylamino)-3-(2-thenoyl)pyridine is further added. The mixture is stirred at 60° C. for 5 hours. After the completion of the reaction, the reaction mixture is poured into ice-water, followed by extraction with ethyl acetate. The extract is washed with water and dried over magnesium sulfate, and then the solvent is distilled off. The residue is converted into the salt with fumaric acid in ethanol. The salt is recrystallized from ethanol to 2-(6-morpholinohexanoylamino)-3-(2-thenoyl)pyridine fumarate, m.p. 143°-145° C. (Decomposition)

EXAMPLE 10

To 10 ml of dimethylformamide are added 1.15 g of 2-amino-3-(4-benzoyl)pyridine and 0.48 ml of pyridine, whereto a solution of 1.1 g of 6-acetylaminohexanoyl chloride in 5 ml of dichloromethane is added dropwise. The mixture is stirred at room temperature for 1 hour. Water is added, and the dichloromethane layer is washed with water. Thereafter, the solvent is distilled off. The residue is crystallized from a mixed solvent of isopropyl ether and methanol to give 2-(6-acetylaminohexanoylamino)-3-(4-chlorobenzoyl)pyridine, m.p. 117°-119° C.

EXAMPLE 11

In 10 ml of toluene is suspended 1.3 g of 60% sodium hydride, whereto 5.3 g of 6-aminohexanol is added dropwise. The mixture is stirred at 70° C. for 1.5 hours. To the mixture is added dropwise a solution of 6.7 g of 2-chloro-3-(2-thenoyl)pyridine in 10 ml of toluene under ice-cooling. The mixture is stirred at 40° C. for 1.5 hours. The mixture is poured into ice-water, whereto toluene is added. The toluene layer is extracted with a dilute hydrochloric acid and the extract is rendered alkaline with potassium carbonate. The isolated oily substance is extracted with chloroform. The extract is washed with water and dried over potassium carbonate, and then the solvent is distilled off. The residue is converted into the salt with maleic acid in ethyl acetate. The salt is recrystallized from a mixed solvent of ethyl acetate and isopropyl alcohol to give 2-(6-aminohexyloxy)-3-(2-thenoyl)pyridine maleate, m.p. 120°-121° C.

EXAMPLE 12

To a solution of 3.5 g of 2-bromopyridine in 20 ml of anhydrous ether is added dropwise 16.9 ml of n-butyllithium at −50° C. to −70° C., and the mixture is stirred for 30 minutes. To the mixture is added dropwise a solution of 4.9 g of 3-cyano-2-(6-dimethylaminohexyloxy)pyridine in 5 ml of anhydrous ether at −50° C. to −60° C. The mixture is stirred for 1 hour. Under ice-cooling, water and ethyl acetate are added thereto. After the ethyl acetate layer is dried over anhydrous magnesium sulfate, the solvent is distilled off. A dilute hydrochloric acid is added to the residue, and stirred at 40° C. for 10 minutes. After the completion of the reaction, the reaction mixture is rendered alkaline with 4N sodium hydroxide and extracted with toluene After the extract is washed with water and dried over anhydrous magnesium sulfate, the solvent is distilled off. The residue is converted into the fumarate in ethanol, and the fumarate is recrystallized from ethanol to give 2-(6-dimethylaminohexyloxy)-3-picolinoylpyridine 3/2 fumarate, m.p. 132°-134° C. (Decomposition)

EXAMPLE 13

In 10 ml of toluene is suspended 1.3 g of 60% sodium hydride, whereto 6.5 g of 6-dimethylaminohexanol is added dropwise. The mixture is stirred at 70° C. for 1 hour. Under ice-cooling, 6.7 g of 2-chloro-3-(2-thenoyl)pyridine is added thereto, and the mixture is stirred at 40° C. for 1 hour. After the completion of the reaction, the reaction mixture is poured into ice-water, whereto toluene is added. The toluene layer is extracted with a dilute hydrochloric acid, and the extract is rendered alkaline with potassium carbonate. The isolated oily substance is extracted with toluene After the extract is washed with water and dried over anhydrous magnesium sulfate, the solvent is distilled off. The residue is converted into the fumarate in isopropyl alcohol, and the fumarate is recrystallized from isopropyl alcohol to give 2-(6-dimethylaminohexyloxy)-3-(2-thenoyl)pyridine 3/2 fumarate, m.p. 104°-105° C. (Decomposition).

EXAMPLE 14

In 20 ml of toluene is suspended 0.6 g of 60% sodium hydride, whereto 3 ml of 2-oxopyrrolidine is added. Under ice-cooling, 2.7 g of 2-(4-chlorobutyrylamino)-3-(2-thenoyl)pyridine is added thereto, and the mixture is stirred at room temperature for 1 hour. The mixture is poured into water, and the solvent of the toluene layer is distilled off. The residue is recrystallized from toluene-isopropyl ether to give 2-(2-oxopyrrolidin-1-yl)-3-(2-thenoyl)pyridine, m.p. 148°-150° C.

EXAMPLE 15

To a suspension of 1.1 g of 60% sodium hydride in 10 ml of toluene is added 5 g of 2-oxopiperidine, followed by addition of 6.4 g of 2-chloro-3-(4-chlorobenzoyl)-pyridine. The mixture is stirred at 90°-100° C. for 5 hours. After water is poured into the reaction mixture, the solvent of the toluene layer is distilled off. The residue is recrystallized from methanol to give 2-(2-oxopiperidino)-3-(4-chlorobenzoyl)pyridine, m.p. 154°-156° C.

EXAMPLE 16

To a suspension of 1.3 g of 60% sodium hydride in 20 ml of toluene is added 5.1 g of 2-oxopyrrolidine, followed by addition of 7.4 g of 2-chloro-3-(4-methoxybenzoyl)pyridine. The mixture is stirred at 50° C. for 1 hour. After the reaction mixture is poured into water, the toluene layer is washed with water and the solvent thereof is distilled off. The residue is recrystallized from a mixed solvent of isopropyl ether and ethyl acetate to give 3-(4-methoxybenzoyl)-2-(2-oxopyrrolidin-1-yl)pyridine, m.p. 76°-77° C.

The following compounds can be obtained in the same manner as in the foregoing Examples.

(17) 2-[2-(6-Dimethylaminohexylthio)-1-methylethylthio]-3-(2-thenoyl)pyridine oxalate, m.p. 94°-97° C.

(18) 2-(6-Dimethylaminohexylthio)-6-methyl-3-(2-thenoyl)pyridine 3/2 fumarate, m.p. 99°-100° C.

(19) 2-[2-(6-Dimethylaminohexylthio)ethylthio]-3-(2-thenoyl)pyridine oxalate, m.p. 92°-95° C.

(20) 2-[2 (3-Dimethylaminopropylthio)-1-methylethylthio]-3-(2-thenoyl)pyridine oxalate, m.p. 85°-88° C.

(21) 2-(6-Dimethylaminohexylthio)-6-isopropyl-3-(2-thenoyl)pyridine oxalate, m.p. 135°-137° C.

(22) 2-(6-Diethylaminohexylthio)-6-isopropyl-3-(2-thenoyl)pyridine oxalate, m.p. 107°-109° C.

(23) 2-[4,5-Dichloro-2-(2-dimethylaminoethoxy)phenoxy]-3-(3-phenylpropionyl)pyridine maleate, m.p. 167°-168° C.

(24) 2-[4,5-Dichloro-2-(3-dimethylaminopropoxy)phenoxy]-3-(3-(4-chlorophenyl)propionyl)pyridine fumarate, m.p. 160°-161° C.

(25) 3-(4-Chlorocinnamoyl)-2-[4,5-dichloro-2-(2-diethylaminoethoxy)phenoxy]pyridine hydrochloride, m.p. 170°-172° C.

(26) 3-(4-Chlorocinnamoyl)-2-[4,5-dichloro-2-(3-dimethylaminopropoxy)phenoxy]pyridine ½ fumarate, m.p. 166°-167° C.

(27) 3-(1-Oxo-5-phenyl-2,4-pentadienyl)-2-[4,5-dichloro-2-(2-dimethylaminoethoxy)phenoxy]pyridine hydrochloride 1 hydrate, m.p. 187°-188° C.

(28) 3-(3-Nitrocinnamoyl)-2-[4,5-dichloro-2-(2-dimethylaminoethoxy)phenoxy]pyridine hydrochloride 1 hydrate, m.p. 194°-195° C.

(29) 2-[4,5-Dichloro-2-(2-dimethylaminoethoxy)phenoxy]-3-(4-methoxycinnamoyl)pyridine hydrochloride, m.p. 208°-209° C.

(30) 3-(2-Chlorocinnamoyl)-2-[4,5-dichloro-2-(2-dimethylaminoethoxy)phenoxy]pyridine hydrochloride, m.p. 172°-174° C.

(31) 3-Cinnamoyl-2-[2-(2-dimethylaminoethoxy)phenoxy]pyridine maleate, m.p. 125°-126° C.

(32) 2-[4-(2-Dimethylaminoethoxy)phenoxy]-3-(2-thenoyl)pyridine ½ fumarate ¼ hydrate, m.p. 124°-126° C.

(33) 2-(4-Dimethylaminomethylphenoxy)-3-(2-thenoyl)pyridine fumarate, m.p. 130°-132° C.

(34) N,N-dimethyl-4-[3-(2-thenoyl)-2-pyridyloxy]-phenoxyacetoamide, m.p. 106°-109° C.

(35) Ethyl 4-[3-(2-thenoyl)-2-pyridyloxy]phenoxyacetate, m.p. 88°-89° C.

(36) 4-[3-(2-Thenoyl)-2-pyridyloxy]phenoxyacetic acid, m.p. 163°-166° C.

(37) 2-[2-(6-Dimethylaminohexyloxy)phenoxy]-3-(2-thenoyl)-pyridine maleate, m.p. 123°-125° C.

(38) 2-(6-Dimethylaminohexyloxy)-3-(4-chlorobenzoyl)-pyridine 3/2 fumarate, m.p. 135°-137° C.

(39) 2-(6-Dimethylaminohexyloxy)-3-(4-fluorobenzoyl)-pyridine maleate, m.p. 101°-103° C.

(40) 2-(4-Diethylamino-1-methylbutylamino)-3-(4-fluorobenzoyl)pyridine oxalate, m.p. 80°-82° C.

(41) 2-(6-Dimethylaminohexyloxy)-6-methyl-3-(2-thenoyl)-pyridine maleate, m.p. 87°-89° C.

(42) 2-(6-Dimethylaminohexyloxy)-3-(5-methyl-2-thenoyl)-pyridine 3/2 fumarate, m.p. 153°-155° C.

(43) 2-(4-Diethylamino-1-methylbutylamino)-3-(2-thenoyl)-pydirine oxalate, m.p. 98°-102° C.

(44) N-(3-benzoyl-5-chloro-2-pyridyl)-4-(2-oxopyrrolidin-1-yl)butylcarboxamide, m.p. 88°-89° C.

(45) N-[3-(4-chlorobenzoyl-2-pyridyl)]-4-(2-oxopyrrolidin-1-yl)butylcarboxamide, m.p. 179°-181° C.

(46) N-[3-(2-thenoyl)-2-pyridyl]-6-acetylaminohexanamide, m.p. 107°-110° C.

(47) N,N-dimethyl-6-[3-(2-thenoyl)-2-pyridylthio]-hexanamide, m.p. 37°-39° C.

(48) 6-Dimethylamino-N-[3-(2-thenoyl)-2-pyridyl]-hexanamide maleate, m.p. 137°-138° C.

(49) 2-(6-Dimethylaminohexyloxy)-3-nicotinoylpyridine 3/2 fumarate, m.p. 127°-131° C.

(50) 2-(6-Dimethylaminohexyloxy)-3-(2-furoyl)pyridine oxalate, m.p. 115°-118° C.

(51) 2-(6-Dimethylaminohexyloxy)-3-(3-thenoyl)-2-pyridine 3/2 fumarate, m.p. 109°-111° C.

(52) 2-(6-Dimethylaminohexyloxy)-3-(4-hydroxy-3,5-di-t-butylbenzoyl)pyridine fumarate, m.p. 149°-150° C.

(53) 2 (6-Dimethylaminohexyloxy)-3-(3,4-dimethoxybenzoyl)-pyridine, m.p. 60°-61° C.

(54) 2-(6-Dimethylaminohexyloxy)-3-(4-methylthiobenzoyl)-pyridine, m.p. 67°-68° C.

(55) 6-(N-benzyl-N-methylamino)-N-[3-(2-thenoyl)-2-pyridyl]-hexanamide fumarate, m.p. 142°-144° C.

(56) 3-(4-Chlorobenzoyl)-2 (2-oxopyrrolidin-1-yl)pyridine, m.p. 125°-127° C.

(57) 2-(2-Oxopyrrolidin-1-yl)-5-(4-chlorobenzoyl)-pyridine, m.p. 139°-140° C.

(58) 2-(2-Oxopyrrolidin-1-yl)-3-[4-(2-oxopyrrolidin-1-yl)-benzoyl]pyridine, m.p. 149°-150° C.

(59) 2-(2-Oxopyrrolidin-1-yl)-3-(4-chlorobenzoyl)-6-methyl-pyridine, m.p. 154°-156° C.

(60) 2-[4-(6-Dimethylaminohexyloxy)phenylthio]-3-(2-thenoyl)-pyridine fumarate, m.p. 121°-123° C.

(61) N-(2-Dimethylaminoethyl)-4-[3-(2-thenoyl)-2-pyridyloxy]-phenoxybenzamide,

(62) 2-[4-(3-Dimethylaminopropyl)phenoxy]-3-(2-thenoyl)-pyridine

(63) 2-{4-[2-(Pyrrolidin-1-yl)ethoxy]phenoxy}-3-(2-thenoyl)-pyridine, m.p. 103°-105° C.

(64) 2-[4-(2-Morpholinoethoxy)phenoxy]-3-(2-thenoyl)pyridine

(65) 2-{4-[2-(4-Methylpiperazin-1-yl)ethoxy]phenoxy}-3-(2-thenoyl)pyridine

(66) 2-{4-[2-(2-Oxopyrrolidin-1-yl)ethoxy]phenoxy}-3-(2-thenoyl)pyridine

(67) 2-{4-[2-(4-(2-Hydroxyethyl)piperazin-1-yl)propoxy]phenoxy}-3-(2-thenoyl)pyridine

(68) 2-[3-(6-Dimethylaminohexyloxy)phenoxy]-3-(2-thenoyl)-pyridine

(69) 2-[4-(6-Dimethylaminohexyloxy)phenoxy]-3-(3-thenoyl)-pyridine

(70) 2-[4-(2-Dimethylaminoethoxy)phenoxy]-3-(2-furoyl)pyridine

(71) 2-[4-(2-Dimethylaminoethoxy)phenoxy]-3-(2-pyrrolyl-carbonyl)pyridine

(72) 2-[4-(2-Piperidinoethoxy)phenoxy]-3-(2-thenoyl)pyridine

(73) 2-(7-Dimethylaminoheptyloxy)-3-(2-thenoyl)-pyridine

(74) 2-(8-Dimethylaminooctyloxy)-3-(2-thenoyl)pyridine

(75) 2-(1-Methyl-6-dimethylaminohexyloxy)-3-(2-thenoyl)-pyridine

(76) 2-(6-Dimethylaminohexyloxy)-3-(4-methylsulfinylbenzoyl)-pyridine

(77) 6-(2-Methoxycarbonylpyrrolidin-1-yl)-N-[3-(2-thenoyl)-2-pyridyl]hexanamide

(78) 6-(2-Hydroxymethylpyrrolidin-1-yl)-N-[3-(2-thenoyl)-2-pyridyl]hexanamide

(79) 6-(2-Formylpyrrolidin-1-yl)-N-[3-(2-thenoyl)-2-pyridyl]-hexanamide

(80) 2-(6-Dimethylaminohexyloxy)-5-(2-thenoyl)-pyridine

(81) 2-(6-Dimethylaminohexyloxy)-6-phenyl-3-(2-thenoyl)-pyridine fumarate ¼ hydrate, m.p. 146°-149° C.

(82) 2-(6-Dimethylaminohexyloxy)-3-(6-methoxy-2-naphthoyl)-pyridine fumarate 1 hydrate, m.p. 140°-144° C.

(83) 2-(6-Dimethylaminohexyloxy)-3-(2-pyrrolylcarbonyl)-pyridine fumarate, m.p. 148°-150° C.

(84) 2-(6-Dimethylaminohexyloxy)-3-(3-indolylcarbonyl)-pyridine fumarate, m.p. 161°-162° C.

(85) 2-[4-(2-Piperidinoethoxy)phenoxy]-3-(2-thenoyl)pyridine, m.p. 95°-97° C.

(86) 2-(6-Dimethylaminohexyloxy)-3-benzoylpyridine 3/2 fumarate, m.p. 119°-121° C.

(87) 2-(6-Dimethylaminohexyloxy)-5-(4-fluorobenzoyl)pyridine fumarate ¼ hydrate, m.p. 95°-97° C.

(88) 2-(4-Dimethylaminomethylcyclohexylmethoxy)-3-(2-thenoyl)-pyridine fumarate, m.p. 135°-136° C.

(89) 2-(6-Aminohexylthio)-3-(2-thenoyl)pyridine fumarate, m.p. 151°-154° C.

(90) 2-[2-(3-Dimethylaminopropylthio)ethylthio]-3-(2-thenoyl)-pyridine oxalate, m.p. 117°-118° C.

(91) 2-(6-Dimethylaminohexyloxy)-3-(5-formyl-2-thenoyl)-pyridine 3/2 fumarate, m.p. 126°-129° C.

(92) 2-(6-Dimethylaminohexyloxy)-3-(2-thiazolylcarbonyl)-pyridine oxalate, m.p. 137°-138° C.

(93) 2-(7-Dimethylaminoheptyloxy)-3-(2-thenoyl)-pyridine oxalate ¼ hydrate, m.p. 150°-154° C.

(94) 2-(7-Dimethylaminoheptylthio)-3-(2-thenoyl)-pyridine fumarate, m.p. 100°-103° C.

(95) 2-(5-Dimethylamino-1-methylpentyloxy)-3-(2-thenoyl)-pyridine oxalate, m.p. 147°-148° C.

(96) 2-(5-Dimethylamino-1-methylpentylthio)-3-(2-thenoyl)-pyridine oxalate, m.p. 87°-89° C.

(97) 2-(6-Dimethylamino-1-methylhexylthio)-3-(2-thenoyl)-pyridine oxalate ¼ hydrate, m.p. 97°-99° C.

(98) 2-(7-Dimethylamino-1-methylheptylthio)-3-(2-thenoyl)-pyridine oxalate ¼ hydrate, m.p. 96°-99° C.

(99) 2-[2-(3-Dimethylaminopropoxy)ethylthio]-3-(2-thenoyl)-pyridine oxalate, m.p. 132°-135° C.

(100) 2-[2-(6-Dimethylaminohexylthio)-1,1-dimethylethylthio]-3-(2-thenoyl)pyridine oxalate, m.p. 95°-97° C.

(101) 2-(6-Dimethylaminohexylamino)-3-(2-thenoyl)-pyridine oxalate, m.p. 123°-125° C.

(102) 3-(2-Thenoyl)-2-(N,N,N'-trimethyl-6-aminohexylamino)-pyridine 2 hydrochloride, m.p. 189°-191° C. (decomp.)

(103) 2-[3-(2-Dimethylaminoethoxy)propylamino]-3-(2-thenoyl)-pyridine oxalate, m.p. 107°-108° C.

(104) 3-Benzoyl-2-(6-dimethylaminohexylthio)-6-methylpyridine 3/2 fumarate, m.p. 101°-103° C.

(105) 3-Benzoyl-2-[2-(3-dimethylaminopropylthio)-1-methylethylthio]-6-methylpyridine 3/2 fumarate, m.p. 150°-152° C.

(106) 2-(6-Dimethylaminohexylthio)-4,6-dimethyl-3-(2-thenoyl)-pyridine oxalate ¼ hydrate, m.p. 151°-152° C.

(107) 6-(3-Thiazolidinyl)-N-[3-(2-thenoyl)-2-pyridyl]-hexanamide oxalate, m.p. 152°-154° C.

(108) 2-(6-Dimethylaminohexylthio)-6-isopropyl-3-(5-methyl-2thenoyl)-pyridine oxalate, m.p. 104°-106° C.

(109) 3-Benzoyl-2-(6-dimethylaminohexylthio)-6-isopropyl-pyridine oxalate, m.p. 129°-132° C. (decomp.).

(110) 2-(6-Dimethylaminohexylthio)-3-(4-chlorobenzoyl)-6-isopropylpyridine oxalate ½ hydrate, m.p. 107°-109° C.

(111) 2-(6-Dimethylaminohexylthio)-6-isopentyl-3-(2-thenoyl)-pyridine fumarate, m.p. 107°-110° C.

(112) 2-(6-Dimethylaminohexylthio)-6-t-butyl-3-(2-thenoyl)-pyridine oxalate, m.p. 131°-133° C.

(113) 2-(6-Dimethylaminohexylthio)-3-(2-thenoyl)-6-isobutylpyridine fumarate 3/2 hydrate, m.p. 79°-81° C.

(114) 2-(6-Dimethylaminohexylthio)-3-(2-thenoyl)-6-isopropoxypyridine (115) 2-(6-Dimethylaminohexylthio)-3-(2-thenoyl)-6-chloropyridine (116) 2-(6-Dimethylaminohexylthio)-3-(5-ethyl-2-thenoyl)pyridine (117) 2-(6-Dimethylaminohexylthio)-3-(5-morpholino-2-thenoyl)-pyridine (118) 2-(6-Dimethylaminohexylthio)-3-(5-methoxycarbonylmethyl-2-thenoyl)pyridine (119) 2-[-6-(4-Bis(4-fluorophenyl)methyl)-piperidinohexylthio]-3-(2-thenoyl)-6-isopropylpyridine (120) 2-[6-(4-Morpholinocarbonylmethyl-1-piperazinyl)hexyl-thio]-3-(2-thenoyl)-6-isopropylpyridine (121) 2-[6-(4-(3-Trifluoromethylphenyl))-1-piperazinyl)hexylthio]-3-(2-thenoyl)-6-isopropylpyridine (122) 2-[6-(4-(3-Trifluoromethylphenyl)piperadano)-hexylthio]3-(2-thenoyl)-6-isopropylpyridine (123) 2-(6-Dipropylaminohexylthio)-3-(2-thenoyl)-6-isopropylpyridine
$^1$H-NMR(CDCl$_3$)δ:0.88 (t, 6H); 1.34 (d, 6H); 1.04-1.90 (m, 12H); 2.34 (t, 2H); 2.36 (t, 4H); 3.06 (m, 1H); 3.20 (t, 2H); 6.90 and 7.70 (each d, 2H); 7.12 (m, 1H); 7.50 and 7.70 (each dd, 2H)

(124) 2-(6-Methylaminohexylthio)-3-(2-thenoyl)-6-isopropylpyridine (125) 2-(6-Ethylaminohexylthio)-3-(2-thenoyl)-6-isopropylpyridine oxalate, m.p. 170°-172° C. (decomp.)

(126) 2-[6-(2-Phenylethylamino)hexylthio]-3-(2-thenoyl)-6-isopropylpyridine oxalate, m.p. 168°-171° C. (decomp.)

(127) 2-[6-(2-Phenylethyl)methylaminohexylthio]-3-(2-thenyl)- 6-isopropylpyridine (128) 2-[6-(4-Benzylpiperidino)hexylthio]-3-(2-thenoyl)-6-isopropylpyridine oxalate, m.p. 113°-115° C.

(129) 2-[6-(4-Dimethylaminopiperidino)hexylthio]-3-(2-thenoyl)-6-isopropylpyridine 2 maleate, m.p. 172° C.

(130) 2-(6-Butylaminohexylthio)-3-(2-thenoyl)-6-isopropylpyridine oxalate, m.p. 166°-167° C.

(131) 2-(6-Isopropylaminohexylthio)-3-(2-thenoyl)-6-isopropylpyridine oxalate, m.p. 135°-138° C.

(132) 2-(6-tert-Butylaminohexylthio)-3-(2-thenoyl)-6-isopropylpyridine oxalate, m.p. 157°-159° C. (decomp.)

(133) 2-[6-(N-Benzyl-N-methylamino)hexylthio]-3-(2-thenoyl)-6-isopropylpyridine oxalate, m.p. 91°-94° C.

(134) 2-[6-(N-(3,4-Dimethoxybenzyl)-N-methylamino)hexylthio]-3-(2-thenoyl)-6-isopropylpyridine oxalate, m.p. 100°-102° C.

(135) 2-(6-Dipropylaminohexylthio)-3-(2-thenoyl)-pyridine oxalate, m.p. 106°-108° C.

(136) 2-(8-Dimethylaminooctylthio)-3-(2-thenoyl)-6-isopropylpyridine (137) 2-[6-(N-(2-Dimethylaminoethyl)-N-methylamino)hexylthio]-3-(2-thenoyl)-6-isopropylpyridine 2 maleate, m.p. 146°-148° C.

(138) 2-(6-Benzylaminohexylthio)-3-(2-thenoyl)-6-isopropylpyridine oxalate, m.p. 188° C.

While the present invention has been described by the foregoing specification including working example and experimental example and so on, the embodiment described herein can be changed and modified in various manners within the scope and the spirit of this invention.

We claim:

1. A pyridine compound of the formula

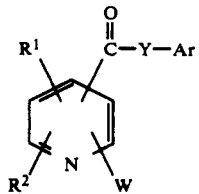

wherein $R^1$ and $R^2$ are the same or different and respectively mean hydrogen, a halogen, a straight-chain or branched chain alkyl having 1 to 8 carbon atoms, a straight-chain or branched chain alkoxy having 1 to 8 carbon atoms, or phenyl or a phenyl which has 1 to 3 substituent(s) selected from among halogens, alkyls, alkoxys, trifluoromethyl, amino, nitro or cyano; Ar means phenyl, naphtyl, or a phenyl or naphthyl which has 1 to 3 substituent(s) selected from hydroxy, 2-oxopyrrolidinyl halogens, alkyls, alkoxys, trifluoromethyl, straight-chain or branched chain alkylthios having 1 to 8 carbon atoms, straight-chain or branched chain alkylsulfinyls having 1 to 8 carbon atoms, straight-chain or branched chain alkylsulfonyls having 1 to 8 carbon atoms, and phenyls and naphthyls which may have 1 to 3 substituents selected from among amino, nitro or cyano; or Ar means furyl, thienyl, pyrrolyl, imidazolyl, oxazolyl, thiazolyl, isoxazolyl, isothiazolyl, pyrazolyl, oxadiazolyl, thiadiazolyl, pyridyl, pyridazinyl, pyrazinyl, indolyl, benzimidazolyl, benzoxazolyl, benzothiazolyl or a furyl, a thienyl, a pyrrolyl, an imidazolyl, an oxazolyl, a thiazolyl, an isoxazolyl, an isothiazolyl, a pyrazolyl, an oxadiazolyl, a thiazolyl, a pyridyl, a pyridazinyl, a pyrazinyl, an indolyl, a benzimidazolyl, a benzoxazolyl or a benzothiazolyl each of which has 1 to 3 substituent(s) selected from among formyl, morpholino, methoxycarbonyl-methyl, halogens, alkyls, alkoxys, trifluoromethyl, alkylthios, alkylsulfinyls, alkylsulfonyls, amino, nitro or cyano; Y means a single bond or a straight-chain or branched chain alkylene having 1 to 8 carbon atoms which may have double bond(s) in the chain; W means a group of the formula

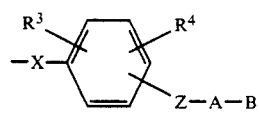

wherein $R^3$ and $R^4$ are the same or different and respectively mean hydrogen, a halogen, a straight-chain or branched chain alkyl having 1 to 8 carbon atoms, a straight-chain or branched chain alkoxy having 1 to 8 carbon atoms, or phenyl or a phenyl which has 1 to 3 substituent(s) selected from among halogens, alkyls, alkoxys, trifluoromethyl, amino, nitro or cyano X means —O—, —S— or —N($R^5$)—, wherein $R^5$ means hydrogen, a straight-chain or branched chain alkyl having 1 to 8 carbon atoms or a straight-chain or branched chain alkanoyl having 2 to 5 carbon atoms; Z means a single bond, —O—, —S—, —N($R^6$)—, wherein $R^6$ means hydrogen, a straight-chain or branched chain alkyl having 1 to 8 carbon atoms or a straight-chain or branched chain alkanoyl having 2 to 5 carbon atoms or —CON($R^7$)—, wherein $R^7$ means hydrogen, a straight-chain or branched chain alkyl having 1 to 8 carbon atoms or a straight-chain or branched chain alkanoyl having 2 to 5 carbon atoms; A means a straight-chain or branched chain alkylene having 1 to 8 carbon atoms; B means an alkoxycarbonyl where the alkoxy moiety in the alkoxycarbonyl is a straight-chain or branched chain alkoxy having 1 to 8 carbon atoms, carboxyl, hydroxyl, —N($R^8$)($R^9$), wherein $R^8$ and $R^9$ are the same or different and respectively mean hydrogen, a straight-chain or branched chain alkyl having 1 to 8 carbon atoms, a hydroxyalkyl where the alkyl moiety in the hydroxyalkyl is a straight-chain or branched chain alkyl having 1 to 8 carbon atoms, a straight-chain or branched chain alkanoyl having 2 to 5 carbon atoms or benzyl, 2-phenyl-ethyl, 1-phenylethyl, 3-phenylpropyl, 4-phenylbutyl, 6-phenylhexyl, 8-phenyloctyl, 2-pyridylmethyl, 3-pyridylmethyl, 4-pyridylmethyl or 2-(2-pyridyl)ethyl, each of which may have 1 to 3 substituent(s) selected from halogens, alkyls, alkoxys, trifluoromethyl, amino, nitro or cyano or R8 and R9 combinedly mean a group forming, taken together with the adjacent nitrogen, 3-thiazolidinyl, 1-pyrrolidinyl, 2-oxo-1-pyrrolidinyl, piperidino, 1-piperazinyl, 1-homopiperazinyl, morpholino or thiomorpholino which may be substituted by formyl, an alkyl, an acyl, benzyl, dimethylamino, 2-hydroxyethyl, methoxycarbonyl, hydroxymethyl, bis(4fluorophenyl)methyl, morpholinocarbonylmethyl or trifluoromethylphenyl or —CON($R^{10}$)($R^{11}$), wherein $R^{10}$ and $R^{11}$ are the same or different and respectively mean hydrogen, a straight-chain or branched chain alkyl having 1 to 8 carbon atoms, a hydroxyalkyl where the alkyl moiety of the hydroxyalkyl is a straight-chain or branched chain alkyl having 1 to 8 carbon atoms, a straight-chain or branched chain alkanoyl having 2 to 5 carbon atoms or benzyl, 2-phenylethyl, 1-phenylethyl, 3-phenylpropyl, 4-phenylbutyl, 6-phenylhexyl, 8-phenyloctyl, 2-pyridylmethyl, 3-pyridylmethyl, 4-pyridylmethyl or 2-(2-pyridyl)ethyl, each of which may have 1 to 3 substituent(s) selected from halogens, alkyls, alkoxys, trifluoromethyl, amino, nitro or cyano or $R^8$ and $R^9$ combinedly mean a group forming, taken together with the adjacent nitrogen, 3-thiazolidinyl, 1-pyrrolidinyl, 2-oxo-1-pyrrolidinyl, piperidino, 1-piperazinyl, 1-homopiperazinyl, morpholino or thiomorpholino which may be substituted by formyl, an alkyl, an acyl, benzyl, dimethylamino, 2-hydroxyethyl, methoxycarbonyl, hydroxymethyl, bis(4-fluorophenyl)methyl, morpholinocarbonylmethyl or trifluoromethylphenyl, or $R^8$ and $R^9$ mean, a group of the formula

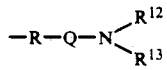

wherein $R^{12}$ and $R^{13}$ are the same or different and respectively means hydrogen, a straight-chain or branched chain alkyl having 1 to 8 carbon atoms, a hydroxyalkyl where the alkyl moiety of the hydroxyalkyl is a straight-chain or branched chain alkyl having 1 to 8 carbon atoms, a straight-chain or branched chain alkanoyl having 2 to 5 carbon atoms, 2-dimethylaminoethyl, phenyl or a phenyl which has 1 to 3 substituent(s) selected from among halogens, alkyls, alkoxys, trifluoromethyl, amino, nitro or cyano or benzyl, 2-phenylethyl, 1-phenylethyl, 3-phenylpropyl, 4-phenylbutyl, 6-phenylhexyl, 8-phenyloctyl, 2-pyridylmethyl, 3-pyridylmethyl, 4-pyridylmethyl or 2-(2-pyridyl)ethyl, each of which may have 1 to 3 substituent(s) selected from halogens, alkyls, alkoxys, trifluoromethyl, amino, nitro or cyano, or combinedly mean a group forming, taken together with the adjacent nitrogen atom, 3-thiazolidinyl, 1-pyrrolidinyl, 2-oxo-1-pyrrolidinyl, piperidino, 1-piperazinyl, 1-homopiperazinyl, morpholino or thiomorpholino, which may be substituted by formyl, an alkyl, an acyl, benzyl, dimethylamino, 2-hydroxyethyl, methoxycarbonyl, hydroxymethyl, bis(4-fluorophenyl)methyl, morpholinocarbonylmethyl or trifluoromethylphenyl; R means —O—, —S(O)$_p$—, wherein p means an integer of 0 to 2, —N($R^{14}$)—, wherein $R^{14}$ means hydrogen, a straight-chain or branched chain alkyl having 1 to 8 carbon atoms or a straight-chain or branched chain alkanoyl having 2 to 5 carbon atoms or —N($R^{15}$)CO—, wherein $R^{15}$ means hydrogen, a straight-chain or branched chain alkyl having 1 to 8 carbon atoms or a straight-chain or branched chain alkanoyl having 2 to 5 carbon atoms; Q means an alkylene having not less than 5 carbon atoms selected from methyltetramethylene, pentamethylene, hexamethylene, octamethylene, decamethylene, dodecamethylene, tetradecamethylene or octadecamethylene, a cyclic alkylene selected from among cyclopropylene, cyclopentylene, cyclohexylene or cyclohexylmethylene, an alkylene having not less than 4 carbon atoms which has an interposing oxygen or a sulfur therein selected from among —CH$_2$O(CH$_2$)$_3$— or —(CH$_2$)$_2$S(CH$_2$)$_3$— or an alkylene having not less than 5 carbon atoms which has a carbonyl group at the terminus selected from among 1-oxohexamethylene, 1-oxooctamethylene or 1-oxodecamethylene, with the proviso that Q means an alkylene having not less than 3 carbon atoms, when R is —N($R^{15}$)CO— or a group of the formula

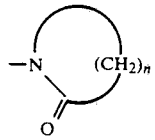

wherein n means an integer of 3 to 5, or a salt thereof.

2. The compound as claimed in claim 1,( wherein said compounds are 2-[2-(3-dimethylaminopropyl)-1-methylethylthio]-3-(2-thenoyl)pyridine, 2-(6-dimethylaminohexylthio)-3-(2-thenoyl)pyridine, 2-(7-dimethylaminoheptylthio)-3-(2-thenoyl)pyridine, 2-[2-(3-dimethylaminopropyl)ethylthio]-3-(2-thenoyl)pyridine, 2-[2-(6-dimethylaminohexylthio)ethylthio]-3-(2-thenoyl)pyridine, 2-[2-(6-dimethylaminohexylthio)-1-methylethylthio]-3-(2-thenoyl)pyridine, 2-[2-(6-dimethylaminohexylthio)-1,1-dimethylethylthio]-3-(2-thenoyl)pyridine, 2-(7-dimethylamino-1-methylheptylthio)-3-(2-thenoyl)pyridine, 2-(6-dimethylaminohexylthio)-6-methyl-3-(2-thenoyl)pyridine, 2-(6-diethylaminohexylthio)-6-isopropyl-3-(2-thenoyl)pyridine, 3-benzoyl-2-[2-(3-dimethylaminopropylthio)-1-methylethylthio]-6-methylpyridine, 2-(6-dimethylaminohexylthio)-6-isopropyl-3-(5-methyl-2-thenoyl)pyridine, 2-[6-(N-benzyl-N-methylamino)hexylthio]-3-(2-thenoyl)-6-isopropylpyridine, 2-[6-(N-(3,4-dimethoxybenzyl)-N-methylamino)hexylthio]-3-(2-thenoyl)-6-isopropylpyridine, 2-(6-benzylaminohexylthio)-3-(2-thenoyl)-6-isopropylpyridine, 2-(6-ethylaminohexylthio)-3-(2-thenoyl)-6-isopropylpyridine, 2-[6-(4-benzylpiperidino-hexylthio]- 3-(2-thenoyl)-6-isopropylpyridine, 2-[6-(4-dimethylaminopiperidino)-hexylthio]-3-(2-thenoyl)-6-isopropylpyridine, 2-[6-(2-phenylethylamino)hexylthio)-3-(2-thenoyl)-6-isopropylpyridine and 2-[6-(N-(2-dimethylaminoethyl)-N-methylamino)hexylthio]-3-(2-thenoyl)-6-isopropylpyridine or their pharmaceutically acceptable salts.

3. A pharmaceutical composition which comprises a therapeutically effective amount of the pyridine compound as claimed in claim 1 or 2 with a pharmaceutically acceptable carrier.

* * * * *

UNITED STATES PATENT AND TRADEMARK OFFICE
CERTIFICATE OF CORRECTION

PATENT NO. : 5,001,137
DATED : March 19, 1991
INVENTOR(S) : Takanori OE, et al

It is certified that error appears in the above-indentified patent and that said Letters Patent is hereby corrected as shown below:

Claim 1, column 23, lines 4 and 5, delete "or $R^8$ and $R^9$ mean,";

Claim 1, column 23, line 5, before "a" insert —or W means—.

Claim 1, column 24, line 6, before "a" insert —W means—.

Signed and Sealed this

Twenty-third Day of May, 1995

Attest:

BRUCE LEHMAN

Attesting Officer     Commissioner of Patents and Trademarks